(12) United States Patent
Cameron et al.

(10) Patent No.: US 9,272,081 B2
(45) Date of Patent: Mar. 1, 2016

(54) SELF-ADHESIVE TET COIL HOLDER WITH ALIGNMENT FEATURE

(71) Applicant: HeartWare, Inc., Miami Lakes, FL (US)

(72) Inventors: Allan Cameron, Natick, MA (US); Christopher Page, Cambridge, MA (US)

(73) Assignee: HeartWare, Inc., Miami Lakes, FL (US)

( * ) Notice: Subject to any disclaimer, the term of this patent is extended or adjusted under 35 U.S.C. 154(b) by 94 days.

(21) Appl. No.: 13/915,332

(22) Filed: Jun. 11, 2013

(65) Prior Publication Data

US 2013/0331638 A1 Dec. 12, 2013

Related U.S. Application Data

(60) Provisional application No. 61/658,178, filed on Jun. 11, 2012.

(51) Int. Cl.
*A61M 1/12* (2006.01)

(52) U.S. Cl.
CPC .................... *A61M 1/127* (2013.01)

(58) Field of Classification Search
USPC .......................................... 607/60
See application file for complete search history.

(56) References Cited

U.S. PATENT DOCUMENTS

| | | | |
|---|---|---|---|
| 5,715,837 A | 2/1998 | Chen | |
| 5,948,006 A | 9/1999 | Mann | |
| 7,574,262 B2* | 8/2009 | Haugland et al. | 607/49 |
| 2008/0147146 A1 | 6/2008 | Wahlgren et al. | |
| 2009/0270951 A1* | 10/2009 | Kallmyer | 607/61 |

FOREIGN PATENT DOCUMENTS

WO    WO 2009/029977 A1    3/2009

OTHER PUBLICATIONS

International Search Report issued by the International Searching Authority (ISA/US) on Sep. 13, 2013 in connection with International Application No. PCT/US2013/045174.
Written Opinion of the International Searching Authority issued by the International Searching Authority (ISA/US) on Sep. 13, 2013 in connection with International Application No. PCT/US2013/045174.

* cited by examiner

*Primary Examiner* — Alyssa M Alter
(74) *Attorney, Agent, or Firm* — Lerner, David, Littenberg, Krumholz & Mentlik, LLP

(57) ABSTRACT

An alignment device for an external coil in a transcutaneous energy transfer (TET) system. The device may be adhered to the skin or clothing of a patient and may ensure alignment between an external coil and an internal coil to provide optimal energy transfer in a TET system.

19 Claims, 5 Drawing Sheets

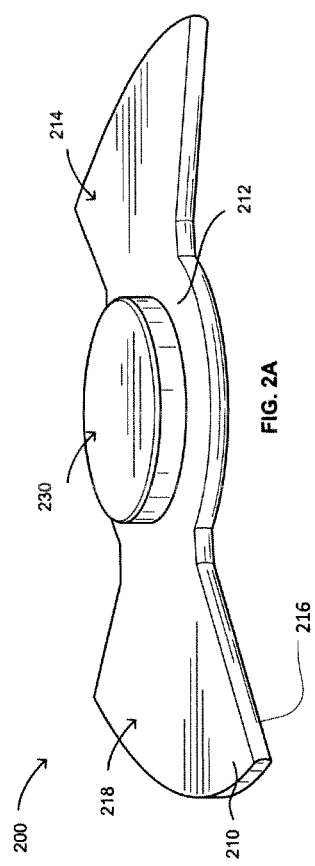
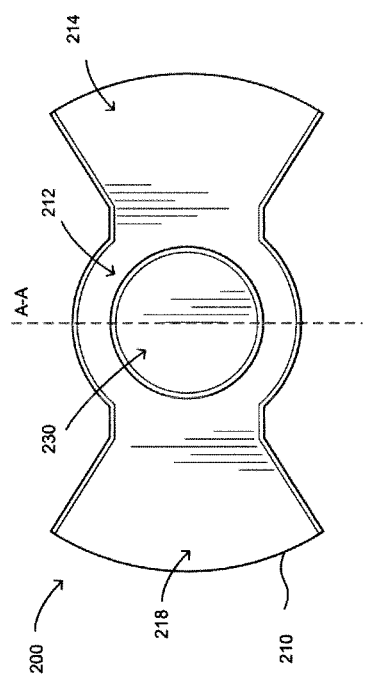

SELF-ADHESIVE TET COIL HOLDER WITH ALIGNMENT FEATURE

CROSS-REFERENCE TO RELATED APPLICATIONS

The present application claims the benefit of the filing date of U.S. Provisional Patent Application No. 61/658,178, filed Jun. 11, 2012, the disclosure of which is hereby incorporated herein by reference.

BACKGROUND OF THE INVENTION

The present invention relates to an alignment device for an external coil in a transcutaneous energy transfer (TET) system.

Certain medical devices implanted within the body must be supplied with electrical power. For example, ventricular assist devices used to supplement the pumping action of the heart must be supplied with power, typically a few watts to tens of watts. This power can be supplied through a wire penetrating the skin. However, such a wire poses a risk of infection, particularly when left in place for months or years. Measures to alleviate this risk add to the burden placed upon the patient and caregivers. TET systems transmit power into the body without the use of wires penetrating the skin, and thus avoid these risks. In certain TET systems, an internal coil and an external coil are provided, the internal coil being implanted within the body of a patient. The internal and external coils include coiled conductors. An alternating current is provided to the external coil, thereby inducing an alternating magnetic field which penetrates the skin and impinges on the internal coil to induce an alternating current in the internal coil. This current may be used to power devices implanted within the body of a patient.

In such a system, the current generated in the internal coil depends directly on the alignment of the internal and external coils. Poor alignment will result in poor energy transmission from the external coil to the internal coil.

SUMMARY OF THE INVENTION

One aspect of the present invention provides an alignment device for a transcutaneous energy transfer coil. The alignment device according to this aspect of the invention desirably includes a structure having an adhesive adapted to adhere to at least one of the skin or clothing of a patient and an engagement feature adapted to engage a housing of a transcutaneous energy transfer coil so as to hold the housing in predetermined alignment with the structure. The structure may include a flexible sheet element bearing the adhesive and a body connected to the sheet element, the body defining the engagement feature. For example, the adhesive may be on a first side of the sheet element and the body may project from the second side of the sheet element. The engagement feature may include a peripheral wall of the body, the peripheral wall extending in an outward direction away from the sheet element.

A further aspect of the invention provides a transcutaneous energy transfer system including an alignment device as discussed above, an interior coil adapted for mounting within the body of the patient, and an external coil having a housing, the housing being adapted for engagement with the engagement feature of the alignment device so that when the internal coil is disposed within the body of the patient and the alignment device is secured on the patient in a predetermined spatial relationship with the internal coil, engagement of the housing with the engagement feature of the alignment device will align the external coil with the internal coil.

Yet another aspect of the invention includes methods of providing energy to an internal coil disposed within the body of a mammalian subject. A method according to this aspect of the invention desirably includes maintaining an alignment device adhesively secured to the skin of the subject or to clothing worn by the subject so that the alignment device is in a predetermined spatial relationship with the internal coil. The method may further include engaging a housing of an external coil with the alignment device to thereby align the external coil with the internal coil. While the housing is engaged with the alignment device, the external coil may be actuated to thereby drive the internal coil. The method may further include of removing the housing of the external coil from the alignment device and subsequently re-engaging the housing in engagement with the alignment device. Untrained personnel, such as the patient or a lay caregiver, may perform the steps of engaging and disengaging the external coil and the alignment device and still be assured of obtaining acceptable alignment of the external coil with the internal coil.

These and other aspects of the invention will be more readily understood with reference to the detailed description taken below.

BRIEF DESCRIPTION OF THE DRAWINGS

FIG. 2A is a perspective view of an alignment device according to a first embodiment;

FIG. 2B is a top view of the alignment device of FIG. 2A;

DETAILED DESCRIPTION

Figure 1:
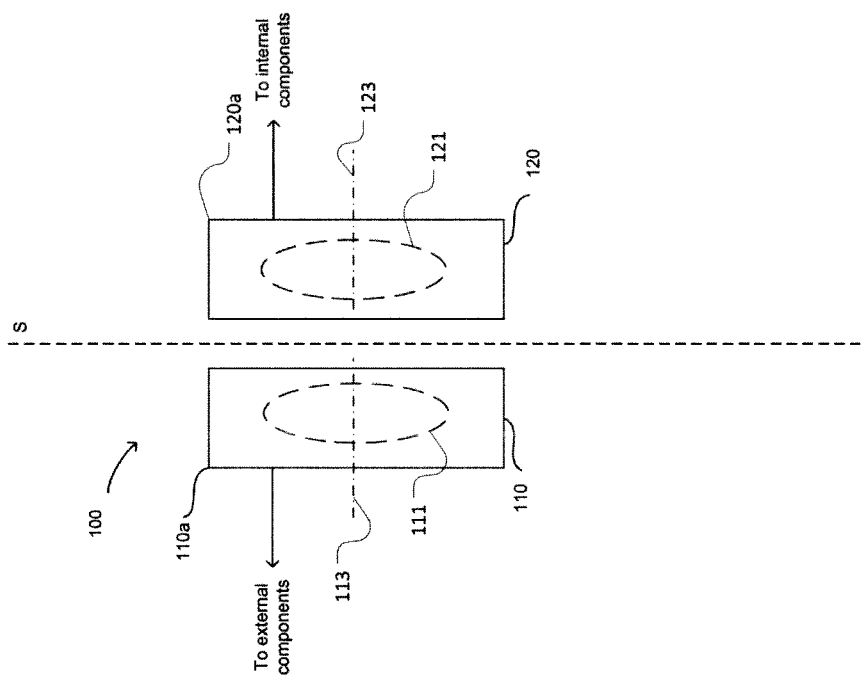
FIG. 1 is a block diagram of a transcutaneous energy transfer (TET) system.
Figure 2C:
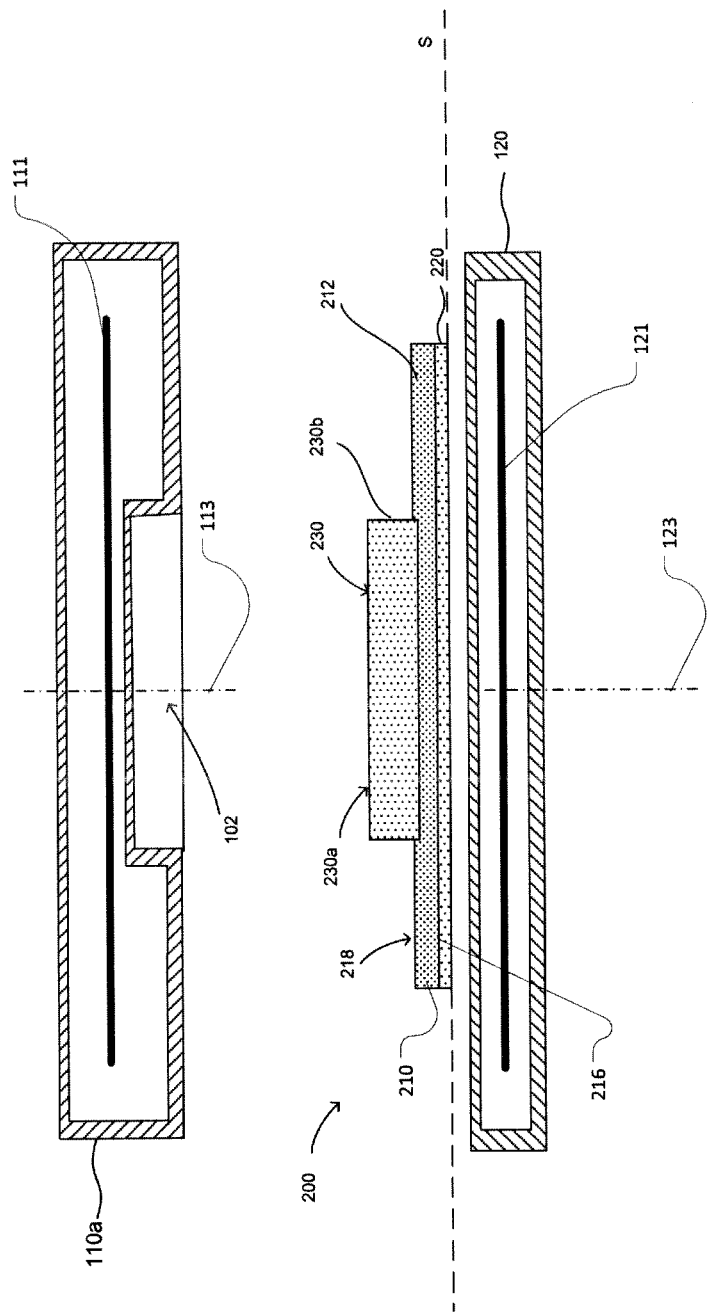
FIG. 2C is a cross-sectional view of the alignment device of FIG. 2A along A-A with an internal and external coil.

A typical TET system 100 (FIG. 1) may include an external coil 110 and an internal coil 120. The external coil 110 may be positioned outside the skin S of a body, such as a mammalian body or the body of a human patient, and the internal coil 120 may be implanted within the body. The external coil 110 includes a housing 110*a* which housing a coiled conductor schematically shown at 111, whereas the internal coil 120 includes a housing 120*a* holding a coiled conductor 121 to allow for energy to be transferred from the external coil 110 to the internal coil 120. Conductor 111 extends around an external coil axis 113, whereas internal coil extends around an internal coil axis 123. Each of the coiled conductors may be generally in the form of a loop, spiral or spiral extending generally in a plane perpendicular to the coil axis, or in the form of a helix extending generally along a cylinder coaxial with the coil axis, or in another form, depending on the number of revolutions of the coiled conductor. As best seen in sectional view (FIG. 2C), the housing 110*a* defines a feature in the form of a generally cylindrical recess 102 coaxial with the external coil axis 113. The internal and external coil housings may also hold additional components (not shown) such as power semiconductors for controlling or rectifying currents flowing in the coils, and signaling components such as RF transmission and receiving components to enable communication between the internal and external components.

The external coil 110 may be connected directly or indirectly to additional external components, such as one or more power sources and/or additional signal processing circuitry. The internal coil 120 may also be connected directly or indirectly to internal components, such as a heart pump, one or more batteries, and/or additional signal processing and control circuitry. The internal coil can be connected to the internal components may be connected by a wired or wireless connection.

For optimum power transfer between the internal and external coils, the external coil should be in a predetermined disposition relative to the internal coil. In the system depicted, that predetermined disposition is one in which the external coil axis 113 is coaxial with the internal coil axis.

An alignment device 200 according to one embodiment of the invention (FIGS. 2A and 2B) includes a flexible sheet element 210 formed of a material such as a polymeric film, a textile fabric, a foam or other suitable materials and combinations of materials. For example, the flexible sheet element may be formed from materials similar to those used in bandages. Sheet element 210 includes a central portion 212 and two peripheral portions 214. Although the combination of the central portion 212 and peripheral portions 214 are shown as having a generally bowtie shape, the sheet element 210 may have other shapes as discussed below. The sheet element 210 has a first side 216 and an oppositely-facing second side 218. The first side 216 has art adhesive 220 thereon. In the particular embodiment depicted, the adhesive 220 (FIG. 2C) covers the entire first side, and thus covers the first side at the central portion 212 of the sheet element 210 and at the peripheral portions 214. However, the adhesive may cover less than all of the first side. Adhesive 216 desirably is selected so that it is compatible with the skin. For example, the adhesives commonly used in adhesive bandages can be employed. A protective sheet (not shown) may be provided on the adhesive to cover the adhesive prior to use. Desirably, the protective sheet has surface properties which allow it to be readily peeled away from the adhesive while leaving the adhesive in place on sheet element 210.

The structure of device 200 also includes a disc-shaped body 230 projecting from the second side 218 of the sheet element 210 in the central region 212. Body 230 has a cylindrical peripheral wall 230b. Body 230 may be formed of essentially any material. Body 230 may be formed integrally with the sheet element 210, or may be formed separately and attached to the sheet element by methods such as adhesive bonding, welding or mechanical fasteners. The diameter of body 230 is just slightly less than the interior diameter of the recess 102 in the housing 110a of the external coil, and the height of body 230 above the second side 218 of the sheet element is also just slightly less than the depth of recess 102. Thus, the body 230 defines an engagement feature which is adapted to mechanically engage the recess 102 of the external coil housing.

When the engagement feature 230 is engaged with the engagement region 102, alignment between the external coil 110 and the internal coil 120 disposed within the body of a human may be ensured. The engagement feature 230 and engagement region 102 may have any configuration. For example, as shown, the engagement feature 230 may be substantially disc shaped. In this example, the engagement feature 230 may have a top surface 230a and a sidewall 230b. The top surface 230a may be substantially planar, and may be coplanar with respect to the coiled conductors and perpendicular to the coil axis. Correspondingly, the housing 110a of the external coil 110 may define a substantially disc shaped engagement region 102.

The engagement feature 230 may engage with the engagement region 102 such that the coiled conductors of the internal and external coils 110, 120 are substantially parallel to one another. In other words, both coils 110, 120 will be substantially perpendicular to the coil axis when aligned.

The alignment device 200 may also include a locking mechanism disposed in or on one or both of the engagement feature 230 or the engagement region 102. The locking mechanism may secure the housing 110a of the external coil 110 to the alignment device 200, such that once secured, alignment of the coils 110, 120 may not be disturbed. The locking mechanism may be any type of mechanism to secure the external coil 110 to the alignment device 200, such as a latch, fastener, detent mechanism or the like. In one example, the engagement feature 230 and the engagement region 102 may include corresponding locking features that prevent unintentional disengagement. Such features may include, for example, a projection formed on one of the engagement feature 230 and engagement region 102 and a corresponding recess formed on the other of the engagement feature 230 and engagement region 102. The locking mechanism may be symmetric or asymmetric with respect to the engagement feature 230.

In a method according to one embodiment of the invention, alignment device 200 is secured on the patient in a predetermined spatial relationship with the internal coil 120. In this embodiment, the predetermined spatial relationship is one in which body 230 is coaxial with the internal coil axis 123. The securing step may be performed by a caregiver such as a doctor, nurse, technician or other trained individual, or by the patient. Placement of the alignment device may be guided by knowledge of the internal coil placement. For example, where the internal coil is located within soft tissue and close to the skin, the person placing the alignment device may locate the internal coil by feel. To facilitate placement of the alignment device in the correct location, the patient's skin optionally may be marked as, for example, by tattooing, with marks corresponding to the outline of the sheet element 210 or a portion of such an outline. The marks may be placed in the appropriate location on the skin so that when the sheet element is positioned within the marks, the body 230 will be coaxial with the internal coil axis. Merely by way of example, an imaging procedure or tactile feel may be used to locate the internal coil and guide placement of the marks. Desirably, the marks are permanent for the life span of the internal coil.

Once the device 200 is adhered to the skin, or the clothing, the housing 110a of the external coil 110 may be engaged with the alignment device 200. In this engaged condition, body 230 is nested within recess 102 of the external coil housing, and therefore the coil axis 113 of the external coil is substantially coaxial with the coil axis 123 of the internal coil. The external coil housing may be held in place by measures such as bandages securing the coil housing to the skin. Because the alignment device assures placement of the external coil in the desired spatial relationship with the internal coil, placement of the external coil is simple and readily performed by the patient or by a caregiver without extensive training.

It should be appreciated that the alignment of the coils need not be perfect. For example, the axes of the coils may be offset slightly from one another or tilted slightly relative to one another. The allowable tolerance will depend upon the performance characteristics of the coils. Merely by way of example, certain can provide acceptable energy transfer performance with 1-2 cm or so of radial misalignment or with the external coil tilted on the order of 10 degrees relative to the internal coil. Thus, the external coil should be positioned in the predetermined spatial relationship to the internal coil within a tolerance appropriate from acceptable energy transfer.

While the external coil is engaged, a current may be driven through the external coil to cause energy transfer to the internal coil at a first rate. At any time, the external coil 110 may be removed from engagement with the alignment device 200. This step also may be performed by the patient, without the aid of a medical professional, irrespective of the driving status of external coil 110. For example, the external coil may be removed temporarily when the patient is bathing. While the external coil is removed, there is no appreciable energy transfer to the internal coil. During this period, the device such as ventricular assist device typically will be powered by a battery including in the internal components. A patient may then replace the external coil into engagement with the alignment device 200, without the aid of a medical professional. Once engaged, energy transfer will resume.

In this way, the alignment device 200 may also be removed and replaced from time to time. If marks have been placed on the skin, replacement of the alignment device can be performed without necessitating difficult realignment procedures of the device 200 with respect to the internal coil 120.

In a further embodiment, the alignment device 200 and the internal coil 120 may be aligned magnetically. In this regard, a first magnet may be embedded within or secured to the alignment device 200 and a second magnet may be embedded within or secured to a housing of the internal coil 120. The polarity and placement of the first and second magnets within the device 200 and coil 120 may be such that a magnetic force is strongest between the magnets when an optimal alignment is achieved between the coils 110, 120. This may allow a user to remove the device 200 and replace the device 200 without necessitating difficult realignment procedures.

The features set forth above can be varied. For example, in one variant, the alignment device may be arranged and external coil housing may have releasable locking features which will hold the external coil in place. This will allow mounting of the external coil on the alignment device without the use of bandages or other elements to hold it in place on the body. For example, body 230 of the alignment device may have a diameter slightly larger than the internal diameter of recess 102, so as to provide a tight fit between the recess and the body, but still allow the patient to deliberately pull the housing away from the alignment device. In another variant, the body and the recess may be provided with complimentary mechanical locking features such as screw threads or lugs. In yet another variant, one of the external coil and the body may include a magnet and the other one may include a complimentary magnet or ferromagnetic element so that magnetic attraction will retain the external coil on the alignment device.

In the embodiment discussed above, the engagement feature of the body includes the cylindrical peripheral wall 230b. In other variants, the peripheral wall may be another surface of revolution such as a conically-tapered surface, and the recess in the coil housing may have a matching taper. In other embodiments, the engagement feature is not a surface of revolution.

Figure 4:
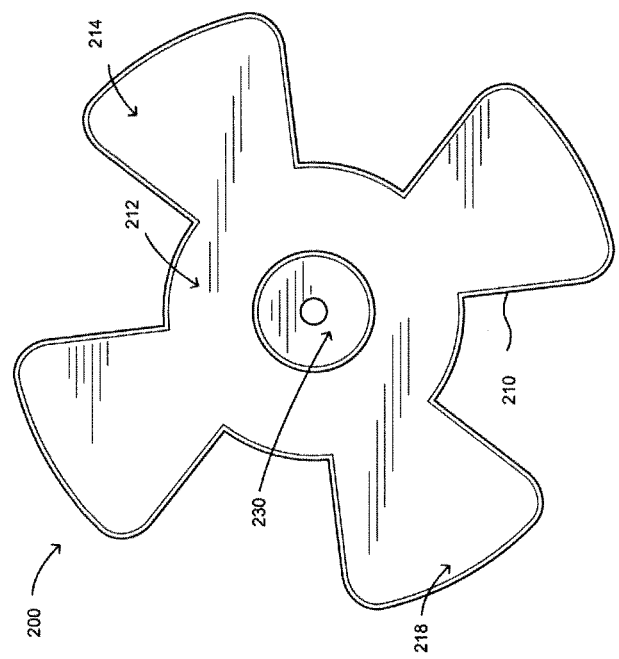
FIG. 4 is a top view of an alignment device according to a third embodiment.
Figure 3:
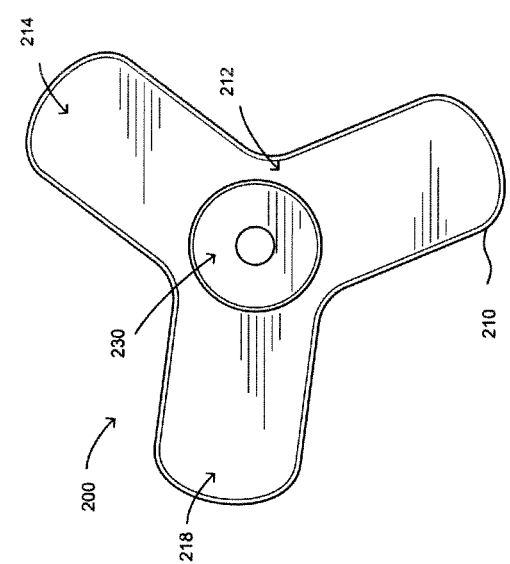
FIG. 3 is a top view of an alignment device according to a second embodiment.
Figure 5:
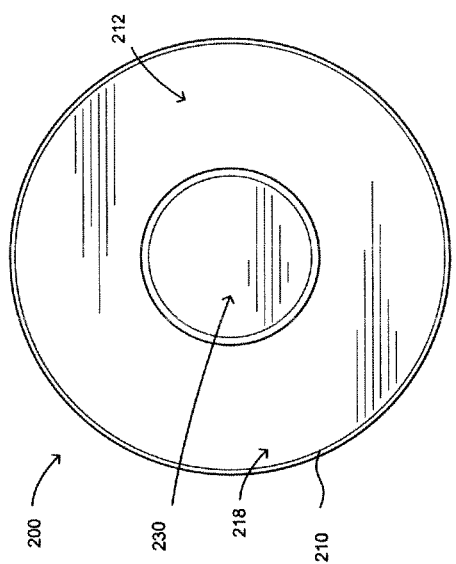
FIG. 5 is a top view of an alignment device according to a fourth embodiment.

In further variants, the sheet element 210 may include only the central portion 212, and may not include the peripheral portions 214. In this regard, the structure 210 may have a substantially circular shape. Additionally or alternatively, the structure 210 may have any number of peripheral portions 214, such as more or less two peripheral portions 214 shown in the figures. Other configurations are shown in FIGS. 3-5. For example, as shown in FIGS. 3 and 4, the sheet element 210 may include more than two peripheral portions 214, such as three or four. Alternatively, as shown in FIG. 5, the structure 210 may not include peripheral portions 214, and may only include a central portion 212. In this example, the sheet element 210 may be substantially circular.

In other arrangements, the engagement features can be varied. For example, the engagement feature may include a recess in the body of the alignment device and a mating protrusion on the body of the external coil. In still other embodiments, the engagement features of the alignment device may include plural elements arrangement to mate with corresponding plural elements of the external coil housing.

In the embodiments discussed above, the alignment device is adhered to the skin of a human being. Alternatively, the alignment device may be adhered to an article of clothing worn by a human being. For example, the alignment device may be adhered to the inside surface of a garment worn by the patient. The position of the alignment device on the garment is selected so that when the patient wears the garment, the alignment device will be disposed in the desired spatial relationship to the interior coil. The garment may be an ordinary shirt or the like, and need not be specially adapted for use with the TET system.

In yet another variant, where the patient's skin is marked with marks bearing a desired spatial relationship to the internal coil, the marks may be used in lieu of the alignment device. Thus, the patient or caregiver may visually align the external coil housing with the marks themselves and secure the external coil housing in place.

As these and other variations and combinations of the features discussed above can be employed, the foregoing description of certain embodiments should be taken as illustrating rather than limiting the present invention.

The invention claimed is:

1. A method of providing energy to an internal coil disposed within the body of a mammalian subject comprising:
   (a) maintaining an alignment device with a protrusion on clothing worn by the subject so that the alignment device is in a predetermined spatial relationship with the internal coil, said protrusion having an exterior sidewall with a first diameter;
   (b) engaging a housing of an external coil with the alignment device by
      (i) aligning the protrusion with a recess formed on the external coil to thereby align the external coil with the internal coil, said recess having an interior sidewall with a second diameter that is slightly smaller than the first diameter; and
      (ii) inserting the protrusion into the recess so as to achieve a tight fit between the exterior sidewall of the protrusion and the interior sidewall of the recess; and
   (c) while the housing is engaged with the alignment device, actuating the external coil to thereby drive the internal coil.

2. A method as claimed in claim 1 further comprising the steps of removing the housing of the external coil from the alignment device and subsequently re-engaging the housing in engagement with the alignment device.

3. A method as claimed in claim 2 wherein the removing and re-engaging steps are performed without the aid of a health care provider.

4. A method as claimed in claim 2 wherein subject is a human patient and the removing and re-engaging steps are performed by the patient.

5. A method as claimed in claim 2 wherein the alignment device is releasably secured on clothing worn by the subject, the method further comprising removing the alignment device from the clothing and subsequently replacing the alignment device with the same or another alignment device.

6. A method as claimed in claim 5 wherein the alignment device is adhesively secured on clothing worn by the subject.

7. A coil holder comprising:
(a) a garment adapted to be worn by a mammalian subject, and
(b) an alignment device having:
(i) a protrusion extending away from the garment to define an exterior sidewall sized for insertion into a recess formed on the housing of a transcutaneous energy transfer coil; and
(ii) a locking mechanism disposed on or adjacent the exterior sidewall to secure the protrusion in the recess, wherein the alignment device is positioned on the garment so that when the subject wears the garment, the alignment device is disposed in a desired spatial relationship with an internal coil mounted under the skin of the subject.

8. The coil holder of claim 7 wherein the alignment device is secured to the garment.

9. The coil holder of claim 7 wherein the alignment device is adhesively secured to the garment.

10. The coil holder of claim 7 wherein the alignment device is positioned adjacent an interior surface of the garment.

11. The coil holder of claim 10 wherein the alignment device is secured to the interior surface of the garment.

12. The coil holder of claim 11 wherein the alignment device comprises a structure with a flexible sheet element that is secured to the interior surface of the garment and the protrusion is connected to the sheet element.

13. The coil holder of claim 12 wherein the sheet element has oppositely-facing first and second sides, further comprising an adhesive disposed on at least a part of the first side, the adhesive being adapted to secure the sheet element to the garment.

14. The coil holder of claim 7 wherein the transcutaneous energy transfer coil defines a coil axis and the recess has an interior sidewall in the form of a surface of revolution about the coil axis.

15. The coil holder of claim 14 wherein the recess extends into a portion of the housing of the transcutaneous energy transfer coil along the coil axis.

16. A method of positioning a medical device adjacent the skin of a mammalian subject comprising:
(a) wearing a garment having an alignment device with protrusion extending away from the garment, the alignment device being positioned so that when the subject wears the garment, the alignment device is disposed in a desired spatial relationship with an internal coil mounted under the skin of the subject;
(b) inserting the protrusion into a recess formed in the a housing of an external coil to thereby align the external coil with the internal coil; and
(c) securing the protrusion in the recess so as to hold the external coil in a fixed position relative to the alignment device.

17. A method as claimed in claim 16 wherein subject is a human patient and the wearing and engaging steps are performed by the patient.

18. A method as claimed in claim 16 wherein the alignment device is adhesively secured to the garment.

19. A method as claimed in claim 16 wherein the protrusion is secured in the recess by a locking mechanism disposed on or adjacent to an exterior sidewall of the protrusion.

* * * * *